United States Patent [19]
Yafuso et al.

[11] Patent Number: 4,886,338
[45] Date of Patent: Dec. 12, 1989

[54] OPTICAL FIBER EVENT SENSOR

[75] Inventors: Masao Yafuso, El Toro; Henry K. Hui, Irvine, both of Calif.

[73] Assignee: Minnesota Mining and Manufacturing Company, St. Paul, Minn.

[21] Appl. No.: 256,305

[22] Filed: Oct. 11, 1988

Related U.S. Application Data

[62] Division of Ser. No. 917,913, Oct. 10, 1986, Pat. No. 4,798,738.

[51] Int. Cl.$^4$ .......................... G02B 6/02; A61B 5/00; C09B 67/00; G01N 33/48
[52] U.S. Cl. .............................. 350/96.29; 350/96.10; 350/96.34; 128/633; 128/634; 128/636; 250/227; 250/237 R; 8/541; 8/562; 8/593; 356/39; 422/55; 422/57
[58] Field of Search .............. 350/96.10, 96.29, 96.30, 350/96.34; 128/633, 634, 635, 636; 8/541, 543, 562, 588, 647, 593; 356/39, 40; 250/227, 237 R; 422/55, 56, 57, 58

[56] References Cited

U.S. PATENT DOCUMENTS

| | | | |
|---|---|---|---|
| Re. 31,879 | 5/1985 | Lübbers et al. | 436/133 |
| 4,200,110 | 4/1980 | Peterson et al. | 128/634 |
| 4,321,057 | 3/1982 | Buckles | 356/445 |
| 4,476,870 | 10/1984 | Peterson et al. | 128/634 |
| 4,557,900 | 12/1985 | Heitzmann | 422/55 |
| 4,560,248 | 12/1985 | Cramp et al. | 350/96.34 |
| 4,568,518 | 2/1986 | Wolfbeis et al. | 422/56 |
| 4,600,310 | 7/1986 | Cramp et al. | 350/96.29 |
| 4,682,895 | 7/1987 | Costello | 128/634 X |
| 4,712,865 | 12/1987 | Hsu et al. | 128/634 X |
| 4,752,115 | 6/1988 | Murray, Jr. et al. | 350/96.29 |
| 4,785,814 | 11/1988 | Kane | 128/634 |
| 4,796,633 | 1/1989 | Zwirkoski | 128/634 |
| 4,798,738 | 1/1989 | Yafuso et al. | 427/2 |
| 4,824,789 | 4/1989 | Yafuso et al. | 128/634 X |

OTHER PUBLICATIONS

Gehrich et al., "Optical Fluorescence and It's Application...", IEEE Trans. on Biomed. Eng., vol. BME-33, No. 2, 2/86, pp. 120-122.

Primary Examiner—John D. Lee
Assistant Examiner—Brian M. Healy
Attorney, Agent, or Firm—Gordon L. Peterson; Frank J. Uxa, Jr.

[57] ABSTRACT

A micro pH sensor is constructed by reacting powdered aminoalkylated cellulose with a dye to covalently bond the dye to the aminoalkyl groups on the cellulose. Any excess unreacted aminoalkyl groups are blocked with a blocking agent and the dye containing powdered cellulose is taken up in a solvent. A portion of the solvated dye containing cellulose is deposited in association with an optical fiber. The cellulose is regenerated into a solid matrix by acid treatment of the solvated dye containing cellulose to deposit the dye containing celllulose matrix on the optical fiber.

11 Claims, 1 Drawing Sheet

OPTICAL FIBER EVENT SENSOR

This application is a division of application Ser. No. 917,913, filed 10/10/86 U.S. Pat. No. 4,798,738.

BACKGROUND OF INVENTION

This invention is directed to an event sensor, as for instance a pH sensor and a process for the preparation of such a sensor. The sensor utilizes a dye which is sensitive to an event. The dye is attached to a finely divided polymeric material as for instance cellulose. The polymeric material, bearing the dye thereon, is dissolved in a solvent and is deposited on an optical surface of an optical fiber. The polymeric material, bearing the dye, is regenerated from the solution to form a solid matrix of the polymeric material, bearing the dye, on the optical surface of the optical fiber.

The determination of an event, as for instance the hydrogen ion concentration or pH of a solution, is very important in many situations. One of theses is the determination of the pH of biological specimens, as for instance, blood. The pH of the blood is indicative of many physiologically important conditions of a patient.

In constructing event sensors it is necessary to construct them of a material which is permeable to an indicator of the event being measured. For a pH sensor, the material must be permeable to ionic species. This severely limits the types of material which may be used for such sensors.

Glass pH electrodes have been used for years for pH determinations. These glass electrodes have to be dipped into a solution for determination of the pH of the solution. In a medical situation, such as a patient recovering from a myocardial infarction, it would be advantageous to be able to measure the pH event in real time, that is continuously. Unfortunately this is not possible with glass electrodes. With glass electrodes, at best, only intermittent measurements can be made. Each of the seperate measurements requires withdrawal of an aliquot of blood from the patient and sending the blood sample to the laboratory for the determination of the pH of the patient's blood. Aside from the requirement of having to continuously withdraw the aliquots of blood, this procedure is time consuming and as such it does not give a true reflection of the patient's condition in real time.

For biological fluids, a prior known sensor uses the fluorescent properties of a dye in conjunction with the ionic permeability of a preformed integral cellulose membrane sheet. In this sensor, the cellulose membrane is chemically treated so as to introduce covalent bondable groups onto the membrane. The dye is then covalently bonded to these groups to adhere the dye to the membrane. A small disk is cut from the membrane sheet and is attached to a cassette in association with an optical fiber bundle also attached to the cassette. When the dye is excited by excitation light imposed on the dye along the fibers, it under goes fluorescence, emitting a wavelength of light at a different wavelength than the excitation wavelength. The emission light is measured as an indication of the pH.

In constructing the above sensor, it is important to insure that the dye is evenly distributed across the membrane sheet such that there will be reproducibility between individual disks cut from the membrane sheet. Aside from evenly disbursing the dye molecules across the membrane, it is also important to insure that the dye molecules are placed with respect to one another such that there is a sufficient concentration to be responsive to pH changes in the solution being measured. Because of these considerations, it is necessary to perform quality control procedures on each disk cut from the membrane to insure that the distribution of the dye on the cellulose membrane is sufficient to render the individual disk useful as a pH sensor.

The above noted cellulose membranes utilize a commercial cellulose membrane as for instance a cellulose membrane suitable for use as a dialysis membrane. The intact membrane is first treated with cyanogen bromide followed by a condensation with an appropriate amine, for instance hexamethylenediamine. This yields a compound which has a primary amino functional group which is reacted with the dye, to attach the dye to the membrane. This method does not lend itself easily to the fabrication of a microsensor on an optical fiber tip which is on the order of 0.006 inches in diameter.

BRIEF DESCRIPTION

This invention provides a micro sensor for sensing an event such as a pH. The sensor of the invention is capable of being constructed in a size of the size domain of an optical fiber. The sensor of the invention is capable of being easily and inexpensively manufactured.

This can be advantageously accomplished by providing a process of forming a micro sensor which comprises selecting a quantity of finely divided water insoluble ionic permeable hydrophylic polymer having a plurality of attachment sites thereon and reacting the attachment sites on the polymer with a quantity of an event sensitive dye so as to attach the dye to at least some of the attachment sites on the polymer to form a dye bearing polymer. The dye bearing polymer is then dissolved in a solvent. A quantity of the solvated dye bearing polymer is then deposited onto an optical surface of an optical fiber and the dye bearing polymer is regenerated from the solvent to form a solid matrix of the regenerated dye bearing polymer on the optical surface of the optical fiber.

In an preferred embodiment, the micro sensor is a pH sensor, the polymer is powdered cellulose and the attachment sites on the cellulose comprise substituent groups on the cellulose. The dye is attached to at least some of the substituent groups on the cellulose to form a dye substituted cellulose. The event sensitive dye is chosen to be a pH sensitive dye. The dye can be attached to the substituent groups on the cellulose by covalently bonding the dye to at least some of the substituent groups on cellulose. Further essentially any substituent groups on the cellulose not having the dye attached thereto can be reacted with a blocking agent so as to render the blocked substituent groups essentially pH insensitive.

In an illustrative embodiment, the substituents groups on the cellulose are $C_2$–$C_{20}$ aminoalkyl groups and the dye is attached to the aminoalkyl groups on the cellulose by covalently bonding the dye to at least some of the aminoalkyl substituents on the cellulose. Essentially any remaining aminoalkyl groups on the cellulose not having the dye attached thereto can be blocked by reacting with a blocking groups so as to render the blocked aminoalkyl groups essentially pH insensitive. The blocking can be accomplished by reacting with an acylating agent such as an acetylating agent.

In an illustrative embodiment the dye is hydroxypyrenetrisulfonic acid or an acceptable salt thereof such as a physiological acceptable salt. This dye is a known dye for use in sensing pH. The dye can be substituted onto the cellulose by reacting the hydroxypyrenetrisulfonic acid to form at least a mono-sulfonyl chloride derivative of the hydroxypyrenetrisulfonic acid and reacting the mono-sulfonyl chloride with the aminoalkylcellulose to attach the dye to the cellulose by forming sulfonamide linkages between the dye and the aminoalkylcellulose. The aminoalkyl cellulose can be aminoethylcellulose.

In an illustrative embodiment, the process can be enhanced by adding a quantity of a permeability enhancing agent to the solution of the dye containing cellulose. The permeability enhancing agent would be selected from small molecular weight water soluble hydrophilic compounds such as sugars, polyols and the like. Suitable for the permeability enhancing agent is glycerol.

When cellulose is used for the polymer it can be regenerated by acid treating the deposited quantity of the solvated dye substituted cellulose located on the optical fiber. This can be accomplished by dipping the deposit of the solvated dye bearing cellulose on the end of the fiber into an acid bath. To enhance the ionic permeability of the sensor, a quantity of glycerol can be added to the acid bath prior to dipping the solvated dye bearing cellulose into the bath.

An illustrative process for forming a pH sensor comprises selecting a quantity of powdered cellulose having a plurality of substituent aminoalkyl groups thereon, reacting the aminoalkyl groups on the cellulose with a quantity of a pH sensitive dye so as to covalently bond the dye to at least some of the aminoalkyl groups on the cellulose to form a dye substituted cellulose, dissolving the dye substituted cellulose in a solvent and depositing a quantity of the solvated dye substituted cellulose onto an optical surface of an optical fiber, and then regenerating the dye substituted cellulose from the solvent by acid treating the deposited quantity of the solvated dye substituted cellulose on the optical fiber to form a solid matrix of regenerated dye substituted cellulose on the optical fiber.

In any of the embodiments of the invention the solid matrix of the regenerated dye bearing polymer, as for instance a cellulose matrix, can be coated with an overcoating. This overcoating would cover the matrix and might extent down over a portion of the optical fiber which is immediately adjacent to the solid matrix.

An advantageous event sensor of the invention includes (a) an optical fiber having an optical surface, (b) a matrix of regenerated polymeric material formed in situ on the optical surface of the optical fiber by depositing a droplet of the polymeric material in solution in a carrier solvent on the fiber and regenerating the polymeric material from the solution by treating the carrier solvent with a regeneration reagent to form the matrix of the polymeric material on the fiber, and (c) a plurality of even sensing dye groups attached to the polymeric material.

BRIEF DESCRIPTION OF THE DRAWINGS

This invention will be better understood when taken in conjunction with the drawing wherein.

Figure 1:
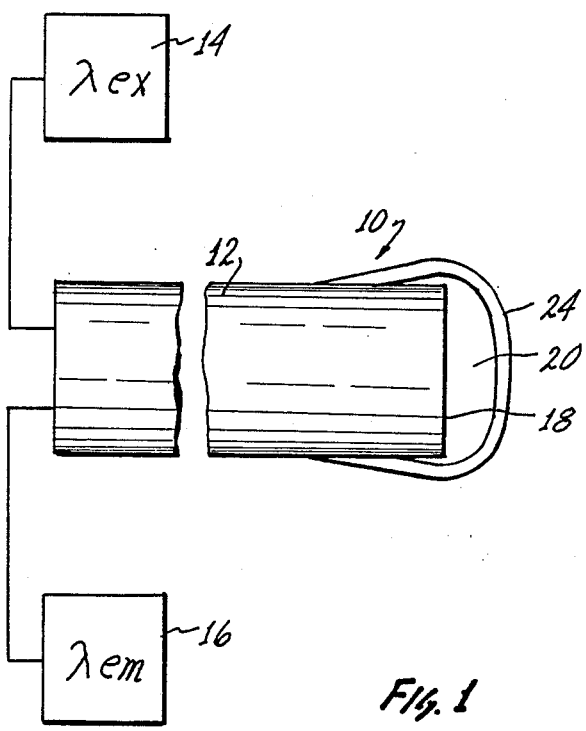
FIG. 1 is cross sectional view of an event sensor of the invention.

This invention utilizes certain principles and/or concepts as are set forth in the claims appended to this specification. Those skilled in the sensor arts will realize that these principles and/or concepts are capable of being utilized in a variety of embodiments which may differ from the exact embodiments utilized for illustrative purposes herein. For these reasons, this invention is not to be construed as being limited to only the illustrative embodiments but should only be construed in view of the claims.

DETAILED DESCRIPTION OF THE PREFERRED EMBODIMENTS

The improved microsensors of the invention are constructed so as to have a even dispersion of a dye throughout a supporting polymeric material. The dye is initially bound to a divided polymeric material. This material is then taken up in solution and a drop of the solution is deposited on an optical surface of an optical fiber. The polymeric material is then regenerated into a solid, forming a matrix on the optical surface of the optical fiber. Dispersed in the matrix is the dye. This allows for the creation of a microsensor having the dye evenly dispersed throughout the matrix of the supporting material.

By utilizing a finely divided polymer and attaching the dye to this finely divided polymer, the finely divided polymer can then be mixed or otherwise homogenized to insure that the dye is evenly dispersed throughout the polymer. This allows for portions of the polymer to be utilized at different instances of time while only requiring a single quality control test on an aliquot of the batch.

In the preferred form of the invention a micro pH sensor is constructed. In order to determine the pH of a solution, as for instance a blood solution, it is important that the supporting polymeric material be water insoluble, such that it is not degraded by the test solution whose pH is being determined. Further it has to be permeable to ions in order for ions from the test solution to cross through the polymer and interact with an appropriate dye located within the interior of a matrix of the polymer.

A further characteristic of the polymer once it has the dye attached thereto is that it must be solubilized so as to be transferable to an optical surface of an optical fiber. Once the polymer with the dye attached thereto is solubilized, a small aliquot of the solution of the polymer with the dye attached thereto can be located on the optical surface of the optical fiber. Regeneration of the solid polymer from the solution then yields a solid matrix of the polymer having the dye located therein, which is correctly positioned on the optical surface of the optical fiber.

The polymer is chosen to be a water insoluble, ionic permeable polymer. Macromolecular hydrophilic polymers which have these general characteristics are useful. Such polymeric material would include cellulose, high molecular weight polyvinylalcohol, (i.e. PVA), polyurethanes, polyacrylamides, polyhydroxyalkyl acrylates, polyvinyl pyrrolidones, hydrophilic polyamides, and polyesters. Generally, for pH sensors, cellulose and high molecular weight polyvinylalcohol would primarily be considered. The polyvinylalcohol would be chosen such that its molecular weight is sufficiently high to render it water insoluble. Solubilization of the polyvinylalcohol would be accomplished via a mixture of water/alcohol as would be appropriate for the particular polyvinylalcohol utilized.

Coupling of the dye to the polymeric material can be accomplished either by direct coupling of the dye to reactive sites on the polymeric material, as for instance, hydroxyl group on either cellulose or polyvinyl alcohol, or through indirect coupling utilizing a substituent group which in itself is coupled to the polymeric material. As, for instance, alkylamines could be first joined to the polymeric material. Thus, for cellulose, an alkylamine would be joined to a hydroxyl group on the cellulose backbone by forming an ether between the alkyl portion of the alkylamine and cellulose backbone. This leaves the amino functionality of the alkylamine available for reaction with the dye to join the dye to the polymeric matrix or backbone.

While the dye could be joined to the polymeric material either directly or through a substituent group utilizing secondary bonding techniques such as hydrogen bonding or the like, it is preferred to form a covalent bond between the dye and the attachment point, either directly on a polymeric material or indirectly through a substituent group. This assures that the dye is fixedly and irreversibly bound to the polymeric material for improved performance of the sensor.

If less than all of the substituent groups are reacted with the dye, the substituent group would be chosen such that either it will not interfere with the measurement being taken or any unreactive substituent group used are capable of being blocked. For instance, if cellulose is utilized and an aminoethyl group is used as the substituent group and the concentration of the dye was chosen such that less than all of the aminoethyl groups are reacted with the dye, the remaining aminoethyl groups are appropriately blocked as, for instance, with an acyl blocking group to essentially neutralize any charge on the unreacted amino groups such that they do not interfere with the measurement being taken, as for instance, a pH measurement.

Generally, suitable for the substituent groups would be $C_2$ to $C_{20}$ aminoalkyls. These aminoalkyl groups could be straight chain, branched chain, cyclo or aromatic. They could include substitution groups located thereon which are hydrophilic such as $-OH$, $-NO_2$, carboxyl, sulfonate or the like. Generally the aminoalkly group will be $C_2$ to $C_8$ with the $C_2$ and $C_3$ aminoalkyl groups being preferred, i.e, aminoethyl or aminopropyl. For ease of blocking of any excess aminoalkyl groups, acetyl can be chosen as a convenient blocking group.

The above noted acyl blocking groups are conveniently utilized for blocking functional groups such as amino groups. Other blocking groups could be utilized to block such amino groups or other functional groups as long as they convert a chargeable species such as the basic amino species of the amino group to a neutral species such that if the sensor is being utilized as a pH sensor, any basic or acidic properties of the substituent groups do not interfere with the pH measurement.

Generally, the starting material for the matrix will be a solid, finely divided polymeric material, as for instance, a powdered material. However, as will be apparent to the art skilled, a different state, as for example a liquid material, could be initially utilized, reacting with the dye and further treated so as to be able to form a solid state material once the dye bearing polymeric material is located on the optical surface of an optical fiber. For convenience however, utilization of a solid powder polymeric material is preferred.

The dye can be added to the polymeric material utilizing either a solid state reaction or a solution reaction. In any event, once the dye is added to the polymeric material, the state of this dye bearing polymeric material should be such that a homogeneous mixture can be formed. As opposed to prior use of membrane sheets which tend to have inconsistencies across the surfaces of the membrane sheet resulting in uneven concentration of the dye on the membrane, by utilizing a polymeric material in a state which allows for homogenization of the dye bearing polymeric material, homogenous properties in the final event sensor can be obtained.

The dye will be chosen such that it is either an absorption dye or a fluorescent dye. For use with a pH sensor, dyes such as hydroxypyrenetrisulfonic acid or its salts, fluorecein or beta-methylumbelliferone can be utilized. These dyes are all very useful for the physiological pH range of blood, as for instance, from about 7.0 to about 8.0. It is recognized that other pH ranges might be chosen as a sensing pH range, or other events other than pH sensing might be chosen. For these other pH ranges or other events, appropriate dyes which are indicative of these events would be chosen, as for instance, if a lower pH range was to be measured, a dye having characteristics of that lower pH range would be chosen.

As noted above, the polymeric material must be susceptible to transmitting ionic species across it such that these ionic species can react with the dye. If a pH sensor is constructed, the pH within the matrix of the sensor itself may not be exactly the same as the pH of the test solution, but it will be such that it tracks the pH of the test solution. Thus, as the pH of the test solution goes up, so does the internal pH within the sensor and as the pH of the test solution goes down, so does the internal pH within the matrix of the sensor.

Once the dye is located on the polymeric material, followed by blocking of any reactive substituent groups or any other groups on the polymeric material if desired, the dye bearing polymeric material is then solubilized in a suitable solvent. The solvent of choice will depend upon the polymeric material itself. In any event, upon solubilization of the dye bearing polymeric material, further homogenization of the dye bearing material takes place by virtue of the solubilization procedure itself.

An appropriate aliquot of the solubilized dye bearing polymeric material is then loaded onto an optical surface of an optical fiber. The solubilized polymeric material is then regenerated so as to form a solid matrix of the dye bearing polymeric material on the optical surface of the optical fiber. Regeneration would depend upon the polymeric material and its solvent. As per the illustrative examples herein, for use with cellulose, a convenient regeneration method is acid regeneration of the cellulose. This is easily accomplished and is easily facilitated for manufacturing reasons by simply adding a drop of a fairly viscous solution of the cellulose material onto the optical surface on the end of an optical fiber and dipping that end of the optical fiber into an acid bath. This regenerates the cellulose matrix forming a solid matrix of the dye bearing regenerated cellulose on the end of the fiber. This is much easier than attempting to adhere a preformed disk or matrix on the very small end of an optical fiber.

If desired, additional solubilized polymeric material can be added to the existing regenerated material already on the optical surface of an optical fiber. The further addition is followed by a further regeneration acid dip. This allows for the build up of a final matrix of a precise dimension. Since the solubilized cellulose adheres to both the regenerated cellulose matrix and to the glass of the optical fiber, it is possible to repeatedly add new aliquots of solubilized cellulose onto the existing regenerated cellulose to stepwise build up a sensor of any desired dimension.

For an illustrative pH sensor of this invention, cellulose will be utilized as the polymeric material. Aminoethylated cellulose is commercially available in a powdered form, as for instance for Sigma Chemical, St. Louis, MO. Normally if commercial aminoethylcellulose is utilized, the material as received from the manufacturer will be first treated to generate free amine groups. This is easily accomplished by simply treating with a sodium bicarbonate solution and drying. The activated aminoethylcellulose should be protected from $CO_2$ in the atmosphere in order to prevent formation of carbonate salts of aminoethylcellulose.

The aminoethylcellulose is then treated with an appropriate dye. For the purposes of illustration of a pH sensor of this invention, hydroxypyrenetrisulfonic acid will be utilized as the dye. It is of course realized that this material could be used as the free acid or as a suitable salt as, for instance as alkali or an alkali earth salts. For use directly within a patient, physiological acceptable salts such the sodium, potassium, calcium or magnesium salts would be used. In any event, the hydroxypyrenetrisulfonic acid hereinafter referred to as HPTS for brevity of this application is first converted into an active species. For use with aminoethylcellulose or other aminoalkylcellulose, a suitable active species would be a sulfonic acid chloride. The HPTS is first acetylated to protect the hydroxy function of the HPTS and then it is converted to a suitable acid chloride. Normally for HPTS, this reaction with aminoethylcellulose will be conducted to yield the mono substituted HPTS.

The acid chloride derivative of the HPTS is reacted with aminoethylcellulose to covalently bond the dye to the cellulose backbone material utilizing sulfonylamido linkages. As is evident from the reaction of an acid chloride with an amine, hydrochloric acid is generated as a byproduct. This byproduct hydrochloric acid tends to react with other amine groups on the aminoethylcellulose. In view of this, the dye can be stepwise reacted with the aminoethylcellulose by first treating with a first batch of the HPTS acid chloride followed by treating this product to convert any amino hydrochlorides back to the free amine groups, and further reacting with additional HPTS acid chloride. It is evident that the desired amount of dye which is to be loaded onto the cellulose can be controlled by either stoichiometric control of the amount of dye which is in fact added to any particular amount of cellulose or by stepwise control by repeated treatments adding first one molecule of the dye and concurrently generating an amine hydrochloride on a further amine group, effectly blocking it against reaction with the dye, followed by regeneration of the free amine from the amine hydrochloride and then adding a second dye group. It is, of course, realized that this could be repeated as many times as is necessary to add increasing amounts of the dye to the aminoethylcellulose.

Once the desired amount of dye is added to the aminoethylcellulose any remaining amino groups are blocked so as to prevent free primary amines from interfering with the pH measurement of the pH sensor. This can be conveniently done by acylating these amines, for instance by utilizing an acetyl blocking group. During acylation a further basic material, for instance pyridine, may be present.

Once the dye has been loaded onto the cellulose, the dye bearing cellulose is then taken up into solution. With cellulose, three basic types of solutions can be formed. The first of these are based on inorganic complexes, the second is based upon organic complexes and the third utilizes hemi esters or sulfur complexes.

For forming inorganic solvents, generally metallic ions such as zinc, copper, nickel, iron, cobalt or cadmium would be utilized. These can be utilized in conjunction with other liquids such as aqueous ethylenediamine.

Typical inorganic solutions for solubilizing a dye bearing cellulose might be copper hydroxide in concentrated ammonia, copper hydroxide in aqueous ethylenediamine, cobalt hydroxide in aqueous ethylenediamine, nickel hydroxide in aqueous ethylenediamine, cadmium hydroxide in aqueous ethylenediamine, nickel hydroxide in concentrated ammonia or iron tartrate in alkali hydroxide.

Typical organic solvents for solubilizing dye bearing cellulose might by $16\frac{1}{2}\%$ methylamine in dimethylsulfoxide, N-methylmorphine N-oxide or quaternary ammonium bases. Suitable hemi esters or half esters would be a hemisuccinate. Suitable complex sulfur intermediates would be the viscose process, dimethylsulfoxide plus carbon disulfide plus an amine or sulfur dioxide in an amine system.

For all of the above solvents the cellulose can be regenerated by acid treatment. Such acid treatment typically would entail utilizing a diluted acid such as the common mineral acids, as, for instance, sulfuric acid.

For increased ion permeability of the final polymeric matrix on the end of the optical fiber, permeability enhancing agents can be added. These generally will be added either in the solvent for the polymeric material, the regeneration solution for the polymeric material or both of these. Suitable for such permeability enhancing material are small molecular weight molecules which are hydrophilic and are water soluble. Such compounds might include sugars and polyol and the like. For instance, glycerol can be added to both a solvent solution for the cellulose and to an acid regeneration bath. Another specific suitable permeability enhancing agents would be low molecular weight water soluble PVA.

After regeneration of the polymeric material on the optical fiber, the dye bearing matrix of the polymeric material on the optical fiber can be overcoated with a suitable coating or overcoating material serving to enhance certain properties of the sensor. An overcoat material would be chosen so as to be ionic permeable as is the polymeric matrix. Suitable for an overcoating material would be cellulose which is impregnated with carbon black or the like.

In use, the sensor on the end of an optical fiber is positioned in the appropriate test solution. If a fluorescent dye is utilized, an excitation light wavelength from a light source is channeled down the fiber toward the sensor. The light strikes the dye, the dyes fluoresces and emits an emission light wavelength. Interaction of the event indicator with the dye modulates the fluorescence. The emission light is then channeled back up the fiber to a light sensor for electrical readout of the same. This procedure is similar to that described in Lubbers et al, U.S. Pat. No. 31,879 and Heitzmann, U.S. Pat. No. 4,557,900. For brevity of this specification, reference is made to these patents for details of this procedure. For this reason, the entire disclosures of Lubbers et al, U.S. Pat. No. 31,879 and Heitzmann, U.S. Pat. No. 4,557,900 are herein incorporated by reference.

To avoid light intensity changes caused by factors other than interaction of the event indicator with the dye, the overcoat is chosen to be opaque to the excitation and emission light wavelengths.

FIG. 1 shows a suitable physical sensor 10 of the invention. An optical fiber 12 is connected to an appropriate light transmitting apparatus 14. The light transmitting apparatus 12 generates the excitation light $\lambda_{ex}$. The optical fiber 12 is also connected to a light receiving apparatus 16. The light receiving apparatus 16 receives and analyzes the emission light $\lambda_{em}$ from the fluorescent dye as is described in the above referenced Lubbers et al and Heinzmann patents.

Located on the optical surface 18 of the fiber 12 is a dye bearing polymeric matrix 20, as for instance, a cellulose matrix containing HPTS as a fluorescent dye therein. The matrix 20 adheres to the optical surface 18 and slightly down along the sides 22 of the end of the fiber 12. An overcoating 24 can then be applied over the totality of the matrix 20 and down further along the side 22 of the fiber 12.

In use, the optical fiber 12 bearing the matrix 20 and the overcoat 24 thereon is placed in an appropriate solution. Excitation light of an appropriate wavelength from the light transmitting apparatus 14 is fed to the fiber 12. This interacts with the dye in the matrix 20 causing the dye to fluoresce. The emission light from the fluorescence is fed to light receiving apparatus 16.

The sensor 10, as is evident from FIG. 1 is of a size domain approximately that of the optical fiber 12. Thus, typically, the sensor 10 would only be slightly larger than a typical 125 micron diameter fiber. The thickness of the matrix 20 would be chosen so as to be approximately three to four mils (0.004 inches) thick.

The following is given as a typical preparation of an event sensor of the invention. For illustrative purposes, a pH sensor utilizing cellulose as the polymeric material and HPTS as the dye will be utilized.

EXAMPLE 1

Activated Aminoethylcellulose 5 grams of aminoethylcellulose is suspended in 100 mls of 2.5% sodium bicarbonate solution. It is stirred for 30 minutes, filtered and rinsed with 50 mls of deionized water. The filter cake is then suspended in 50 mls dry dimethylformamide. It is then filtered and again resuspended in dry dimethylformamide. This dehydrates the filter cake of the activated aminoethylcellulose. If the product is not being utilized immediately, it is stored dry, protected from atmospheric carbon dioxide.

EXAMPLE 2

Acetoxy-pyrenetrisulfonic Acid Trisodium Salt 10 grams of trisodium hydroxypyrenetrisulfonate, 50 mls of acetic anhydride and 1.6 grams of sodium acetate are added to 200 mls of dimethylformamide in a 500 ml flask. The flask is equipped with a condenser having a drying tube and a stirring bar. The contents of the flask are stirred at 50° to 70° C. for one to two hours. The reaction mixture is filtered and the filtrate collected. The filtrate is vacuum evaporated to yield a crude solid product. This crude solid product is extracted into boiling methanol. The volume of the methanol is reduced to 100 mls and cooled. The first batch of product crystallizes out and is filtered. The methanol is again reduced to approximately 20 mls to yield a second crop of product. This is filtered and combined with the first batch and dried for twenty to forty minutes at 60° C.

EXAMPLE 3

Acetoxy-pyrenetrisulfonic Acid Chloride 2 grams of trisodium acetoxy-pyrenetrisulfonate from Example 2, above, and 6.6 grams of phosphorous pentachloride ($PCl_5$) are ground together with a mortar and pestal for 10 minutes. The homogeneous solid mixture is then transferred to a 250 ml round bottom flask fitted with a condenser and drying tube. It is heated in boiling water for 60 minutes. The reaction mixture is then extracted with 200 mls of hot toluene and vacuum filtered. The toluene from the filtrate is stripped off to recover the acetoxy-pyrenetrisulfonic acid chloride.

EXAMPLE 4

HPTS Bearing Aminoethylcellulose 100 mg of acetoxy-pyrenetrisulfonic acid chloride from Example 3 is added to 100 mls of dry dimethylformamide. This is stirred for 45 minutes and 5 grams of activated aminoethylcellulose is added. This mixture is stirred for one hour, filtered and the filter cake washed with 50 mls of dimethylformamide. The filter cake is resuspended in 100 mls of 2.5% sodium bicarbonate solution and stirred for 30 minutes. It is filtered and the filter cake washed twice with 50 ml portions of deionized water. The water is then removed from the filter cake by three washings with dry dimethylformamide. The dried filter cake is then retreated a second time in 100 mls of dimethylformamide with 100 mg of acetoxy-pyrenetrisulfonic acid chloride for 45 minutes. After the second treatment it is filtered and the cake washed with 2.5% sodium bicarbonate followed by two water washes. The product is stored over a dessicant under high vacuum to dry to same.

EXAMPLE 5

Acetylation of Excess Amino Groups on HPTS Bearing Cellulose 3 to 6 grams of the product from Example 4 with 75 mls of acetic anhydride and 1 ml of pyridine is heated one hour at 60° C. The reaction is cooled and filtered. The filter cake is washed with 50 ml portions of sodium bicarbonate solution and then three washes with water. It is dried over a dessicant at high vacuum.

EXAMPLE 6

Inorganic Zinc Based Cellulose Solvent

An inorganic zinc based solvent is prepared by dissolving 4.15 grams of zinc chloride in 100 mls of water. 50 mls of 2.2M sodium hydroxide solution is added dropwise with stirring over ten minutes. The resulting product is centrifuged at 2,000 RPMs in a Beckman TO-6 Centrifuge for ten minutes. The supernatant is decanted and 50 mls of 0.5M sodium hydroxide is added to the precipitate. This is agitated with a glass rod, recentrifuged and decanted again. This procedure is repeated twice more. 50 mls of cold 40% aqueous ethylenediamine and 1 gram of glycerol are added to the final precipitate. This is mixed together by shaking. The product is then blanketed with nitrogen and stored in a refrigerator.

EXAMPLE 7

Solvated HPTS Bearing Cellulose 0.1 gram of acetylated dye bearing aminoethylcellulose from Example 5 above is dissolved by mixing with 1.9 grams of the final solution from Example 6, above, and stored protected from atmospheric carbon dioxide in a freezer overnight. After standing overnight a viscous solution resulted. The solution is further maintain in the freezer until used.

EXAMPLE 8

Regeneralted Cellulose pH Sensor 1 drop of the mixture of Example 7 is added to the end of a clean fiber tip of an optical fiber. This is dipped into a 5% sulfuric acid, 5% glycerol solution for 5 minutes to regenerate the cellulose. The fiber having the regenerated cellulose matrix located thereon is then rinsed with 1% sodium bicarbonate, 5% glycerol solution for 30 seconds. The thickness of the sensor is then measured wet. The desired thickness is 3 to 4 mils when wet. If the sensor is not of the desired thickness, a further drop of the product of Example 7 is added and the sensor is once again dipped into the sulfuric acid, glycerol bath. The sensor is once again washed with sodium bicarbonate and the thickness measured. A further amount of the sensor matrix can be regenerated on the sensor if, again, the desired thickness has not been reached.

Generally the dye will be utilized in a ratio of from about 1 mg of dye to about 20 mg of dye per 1 gram of cellulose. At about 10 mgs of dye per 1 gram of cellulose, a dye molecule is attached to about 5% of the average $NH_2$ sites on the cellulose.

We claim:

1. An event sensor which comprises:
   an optical fiber, said optical fiber having an optical surface;
   a matrix of a regenerated polymeric material;
   a plurality of event sensing dye groups, said event sensing dye groups chemically bound to said polymeric material; and
   said matrix of said regenerated polymeric material formed in situ on said optical surface of said optical fiber.

2. An event sensor of claim 1 wherein:
   said event sensing dye groups are covalently bound to said polymeric material, and said matrix of said regenerated polymeric material is formed by depositing said polymeric material in solution in a carrier solvent on said optical fiber and regenerating said polymeric material from said solution to form said matrix on said optical fiber.

3. An event sensor of claim 2 wherein: said polymeric material is cellulose; and said polymeric material is regenerated by contacting said solution on said optical fiber with an acid solution.

4. At event sensor of claim 3 further including:
   a plurality of substituent groups located on said cellulose; and
   each of said plurality of event sensing dye groups covalently bound to said cellulose by covalently bounding each of said event sensing dye groups to one of said substituent groups.

5. An event sensor of claim 4 wherein:
   said dye is a pH sensitive dye; and
   said event sensor is a pH sensor.

6. An event sensor of claim 1 further including:
   a plurality of substituent groups located on said polymeric material, each of said plurality of event sensing dye groups chemically bound to said polymeric material by chemically bonding each of said event sensing dye groups to one of said substituent groups; and
   a plurality of substituent group blocking groups, said plurality of substituent group blocking groups located on said substituent groups which do not have a dye group attached thereto.

7. An event sensor of claim 1 further including;
   and overcoating, said overcoating comprising cellulose containing an opaque agent in said cellulose, said overcoating covering said matrix on said optical fiber.

8. A pH sensor which comprises:
   an optical fiber, said optical fiber having an optical surface;
   a matrix of a regenerated cellulose formed in situ on said optical surface of said optical fiber by depositing a droplet of cellulose in solution in a carrier solvent on said optical fiber and regenerating said cellulose from said solution by treating said carrier solvent with an acid solution regeneration reagent to form said matrix on said optical fiber;
   a plurality of substituent groups located on said cellulose;
   a plurality of pH sensitive dye groups attached to said cellulose by attaching each of said pH sensitive dye groups to one of said substituent groups; and
   a plurality of substituent group blocking groups located on essentially any of said plurality of substituent groups which does not have a dye group atached thereto.

9. The pH sensor of claim 8 wherein said substituent group blocking groups comprise acylating groups.

10. The pH sensor which comprises:
    an optical fiber, said optical fiber having an optical surface;
    a matrix of a regenerated cellulose formed in situ on said optical surface of said optical fiber by depositing a droplet of cellulose in solution in a carrier solvent on said optical fiber and regenerating said cellulose from said solution by treating said carrier solvent with an acid solution regeneration reagent to form said matrix on said optical fiber;
    a plurality of aminoalkyl groups located on said cellulose;
    a plurality of pH sensitive dye groups attached to said cellulose by attaching each of said pH sensitive dye groups to one of said aminoalkyl groups with sulfonylamido linkage, said plurality of pH sensitive dye groups being less than said plurality of aminoalkyl groups 11. A pH sensor which comprises:
    an optical fiber, said optical fiber having an optical surface;
    a matrix of a regenerated cellulose formed in situ on said optical surface of said optical fiber by depositing a droplet of cellulose in solution in a carrier solvent on said optical fiber and regenerating said cellulose from said solution by treating said carrier solvent with an acid solution regeneration reagent to form said matrix on said optical fiber, said solution further containing glycerol in an amount effective to enhance the permeability of said matrix to ionic species;
    a plurality of substituent groups located on said cellulose; and
    a plurality of pH sensitive dye groups attached to said cellulose by attaching each of said pH sensitive dye groups to one of said substituent groups.

* * * * *

UNITED STATES PATENT AND TRADEMARK OFFICE
CERTIFICATE OF CORRECTION

PATENT NO. : 4,886,338

DATED : Dec. 12, 1989

INVENTOR(S) : Masao Yafuso et al

It is certified that error appears in the above-identified patent and that said Letters Patent is hereby corrected as shown below:

Abstract - 2nd to last line change "celllulose" to -- cellulose --.

Column 1, line 21 change "theses" to -- these --.
Column 3, line 58 change "even" to -- event --.
Column 11, line 56 change "At event" to -- An event --.

Signed and Sealed this

Twenty-fourth Day of December, 1991

Attest:

HARRY F. MANBECK, JR.

*Attesting Officer*  *Commissioner of Patents and Trademarks*